(12) United States Patent
Miettinen et al.

(10) Patent No.: US 10,112,192 B2
(45) Date of Patent: Oct. 30, 2018

(54) PIPETTE COMPRISING IMAGING DEVICE ELEMENT

(71) Applicant: Thermo Fisher Scientific Oy, Vantaa (FI)

(72) Inventors: Juha Miettinen, Vantaa (FI); Mikael Lind, Helsinki (FI); Juha Telimaa, Jarvenpaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 15/317,481

(22) PCT Filed: Jun. 5, 2015

(86) PCT No.: PCT/FI2015/050388
§ 371 (c)(1),
(2) Date: Dec. 9, 2016

(87) PCT Pub. No.: WO2015/189464
PCT Pub. Date: Dec. 17, 2015

(65) Prior Publication Data
US 2017/0120235 A1    May 4, 2017

(30) Foreign Application Priority Data

Jun. 10, 2014    (FI) .................................... 20145531

(51) Int. Cl.
*B01L 3/02* (2006.01)
*G01N 35/10* (2006.01)
(Continued)

(52) U.S. Cl.
CPC ........ *B01L 3/0237* (2013.01); *G01N 35/1011* (2013.01); *H04N 5/23293* (2013.01);
(Continued)

(58) Field of Classification Search
CPC ............. B01L 3/0237; B01L 2200/143; B01L 2300/0654; B01L 2300/027; G01N 35/1011; H04N 5/23293; H04N 7/18
See application file for complete search history.

(56) References Cited

U.S. PATENT DOCUMENTS

| 7,574,929 | B2 | 8/2009 | Telimaa et al. |
| 7,690,274 | B2 | 4/2010 | Telimaa et al. |

(Continued)

FOREIGN PATENT DOCUMENTS

| CN | 1905942 A | 1/2007 |
| CN | 1921945 A | 2/2007 |

(Continued)

OTHER PUBLICATIONS

Finnish Patent and Registration Office, English Machine Translation of Abstract of DE102012102918A1, published Oct. 10, 2013, retrieved from WPI/Thompson, on Jan. 16, 2015 (3 pages).

(Continued)

*Primary Examiner* — Shogo Sasaki
(74) *Attorney, Agent, or Firm* — Wood Herron & Evans LLP

(57) ABSTRACT

A pipette comprising a cylinder with a piston movable inside the cylinder for aspiring and dispensing liquid, and a handle portion for gripping the pipette, wherein the pipette further comprises an imaging device element for obtaining images that assist the use of the pipette.

6 Claims, 4 Drawing Sheets

(51) Int. Cl.
    *H04N 5/232*  (2006.01)
    *H04N 7/18*   (2006.01)

(52) U.S. Cl.
    CPC .......... *H04N 7/18* (2013.01); *B01L 2200/143* (2013.01); *B01L 2300/027* (2013.01); *B01L 2300/0654* (2013.01)

(56) References Cited

U.S. PATENT DOCUMENTS

| | | | |
|---|---|---|---|
| 7,873,269 | B2 | 1/2011 | Toor et al. |
| 8,470,260 | B2 | 6/2013 | Carr et al. |
| 9,782,769 | B2 | 10/2017 | Carr et al. |
| 2006/0133965 | A1 | 6/2006 | Tajima et al. |
| 2009/0055131 | A1 | 2/2009 | Bukshpan et al. |
| 2013/0280143 | A1 | 10/2013 | Zucchelli et al. |
| 2014/0009631 | A1 | 1/2014 | Topliss |

FOREIGN PATENT DOCUMENTS

| | | |
|---|---|---|
| CN | 1956786 A | 5/2007 |
| CN | 103282781 A | 9/2013 |
| DE | 102012102918 A1 | 10/2013 |
| WO | 8400119 A1 | 1/1984 |
| WO | 2005079989 A1 | 9/2005 |
| WO | 2006111977 A2 | 10/2006 |
| WO | 2012069925 A1 | 5/2012 |

OTHER PUBLICATIONS

European Patent Office, English Machine Translation of DE102012102918A1, published Oct. 10, 2013, retrieved from http://translationportal.epo.org, on Jan. 16, 2015 (25 pages).

Finnish Patent and Registration Office, Office Action, Patent Application No. 20145531, dated Jan. 19, 2015 (5 pages).

European Patent Office, International Search Report and Written Opinion of the International Searching Authority, International Application No. PCT/FI2015/050388, dated Sep. 14, 2015 (9 pages).

Chinese Patent Office, First Office Action, Application No. 2015800428445, dated Jun. 6, 2018 (11 pages).

PIPETTE COMPRISING IMAGING DEVICE ELEMENT

CROSS-REFERENCE TO RELATED APPLICATIONS

This application is a submission under 35 U.S.C. § 371 of International Application No. PCT/FI2015/050388, filed Jun. 5, 2015, which claims priority to Finnish Application No. 20145531, filed Jun. 10, 2014, the disclosures of which are hereby expressly incorporated by reference herein in their entireties.

FIELD OF THE INVENTION

The present invention relates to a hand-held pipette intended for use in the dosage of liquids.

BACKGROUND OF THE INVENTION

Pipettes used for liquid dosage in laboratories typically comprise a piston movable in a cylinder for aspiration of liquid into a tip connected with the cylinder. Such pipettes comprise an elongated handle held by palm grip. The volume is usually adjustable. Usually, there is also a mechanism for removing a used tip from the pipette. There also multichannel pipettes comprising, e.g., eight channels in a row. In manual pipettes, all of the operations are carried out by hand force. The piston in almost all manual pipettes is moved by pushing with thumb a spring loaded rod placed at the upper end of the pipette. Volume is usually set by rotating the knob. The detachable tip is removed by pushing a spring loaded push button at the side of the handle.

There are also electronic pipettes in which the piston is actuated by means of an electric motor and a control system associated with it. The tip removal mechanism is still often manual, but there are also electronic pipettes in which also the tip removal mechanism is electrically driven. There are also electronic pipettes in which pistons are actuated by manual force and which comprise an electronic display only. Electronic pipettes have a user interface for selection of the desired pipetting function (e.g., direct or reverse pipetting), setting of the volume and for giving commands for performing operations. The user interface has the necessary switches for input of the necessary settings and performance of the functions. The user interface is connected to a display, by means of which the volume and other necessary data can be displayed. The display can also show menus allowing data input in the control system.

Manual pipettes are described, e.g., in EP 112 887 and electronic pipettes, e.g., in EP 1 725 333. An example of an electronic pipette is Finnpipette® Novus Electronic Pipette (Thermo Fisher Scientific Oy, Finland). This pipette contains also a counter which counts the total number of pipetting operations after the latest calibration. The use may go and check that number and consider whether recalibration is appropriate. After the recalibration, the counter is automatically reset.

High reliability and safety level are important factors in pipetting. A typical user in a laboratory may have to make hundreds of repetitive pipetting series during a working day. The possibility of pipetting errors, e.g., wrong well in a microplate or wrong volume, exists. Pipetting needs also often very accurate movements when liquid is taken from and dispensed into small vessels. This visual task causes extra workload.

SUMMARY OF THE INVENTION

According to the present invention, a pipette is equipped with at least one imaging device element, which is able to monitor the workflow relating to the use of the pipette. The imaging device element may be as a fixed part of the pipette, especially in electronic pipettes, or the imaging device element may be separate module attachable on the pipette, whereby the imaging device element can also be used with manual pipettes without an electronic control system and related interface for operating the pipette.

A pipette is in this context preferably a hand-held entity. The pipette may be used at laboratories for handling liquid samples. Further, the pipette preferably comprises a detachable tip or tip container into which liquid is aspired and from which the liquid is dispensed, connected detachably to the body of the pipette.

An imaging device element is in this context a suitable small-sized device for obtaining an image, preferably in digital form, either as a snapshot or as a continuous image feed, and for forwarding the obtained image to a suitable viewing or analyzing device. The imaging device element can be a single structural element or it can be broken down to a separate parts located at different places in the pipette of the present invention. Examples of the imaging device element are digital cameras, such as disclosed in publications U.S. Patent Application Publication No. 2014/0009631 A1 and U.S. Pat. No. 7,873,269 B2.

In accordance with the present invention it is also possible to save the monitored workflow for later inspection if the correct use of the pipette has to be ensured.

Advantageously, the imaging device of the imaging device element is focused at the area in front of the tip or tips of the pipette, whereby the image provided may be used to guide the pipetting process more precisely, especially when the image shown is magnified view, for example. The imaging device may also or alternatively be focused at the tip or tips of the pipette, whereby the image can be used to help in inserting pipette's tip or tips correctly in small vessels or depressions for aspiring or dispensing small amounts of liquid.

The imaging device element can be used to provide continuous image feed to a suitable display or it can be used to take snapshot images. The continuous image feed is helpful for guiding the actual pipetting operations, for example. The snapshot images can be used for inspection purposes, for example.

The pipette according to the present invention is advantageously provided with integrated or separate display for displaying and viewing the image from the imaging device element. In electronic pipettes the pipette's own display, which may be part of the interface of the electronic pipette, may be used for viewing the image from the imaging device element. In manual pipettes without integrated displays, especially in the cases where the imaging device element is a separate module attached to the pipette, the image from the imaging device element may be viewed in separate display, to which the image from the imaging device element is send by cable or wirelessly, for example.

Advantageously, the pipette according to the present invention is an electronic pipette comprising a motor for moving the piston inside the cylinder, a control system for carrying out pipette operations, and a user interface for operating the pipette. In this kind of electronic pipette, the imaging device element can easily be integrated, and incorporated as a functional component operating and operated through the user interface of the pipette.

The pipette according to the present invention, especially an electronic pipette, is advantageously equipped with image recognition, which can be used to provide different types of automatic warnings and confirmations. For example, the image recognition can be used to recognize whether any liquid is left in the pipette's tip, or if there is a filter missing in the tip, etc. The image recognition can also be used to identify the tip used in the pipette, and this information may be used to set corresponding parameters for the pipette. Further, with the image recognition the pipette's imaging device element can be used to read bar codes or QR codes (Quick Response codes), whereby settings and/or standard work rotations can be easily input in the control system of the pipette.

In a pipette of the present invention, the imaging device element may be connected, or be part of, the handle part or portion of the pipette. Alternatively, the imaging device element may be connected to the pipette via bendable fiber optics wire, which allows easy adjustment of focus area of the digital device element.

The digital imaging device element may comprise a digital camera as the imaging device of the imaging device element.

BRIEF DESCRIPTION OF THE DRAWINGS

Exemplifying embodiments of the present invention and their advantages are explained in greater detail below in the sense of an example and with reference to the accompanying figures, where.

DETAILED DESCRIPTION OF THE INVENTION

Figure 1A:
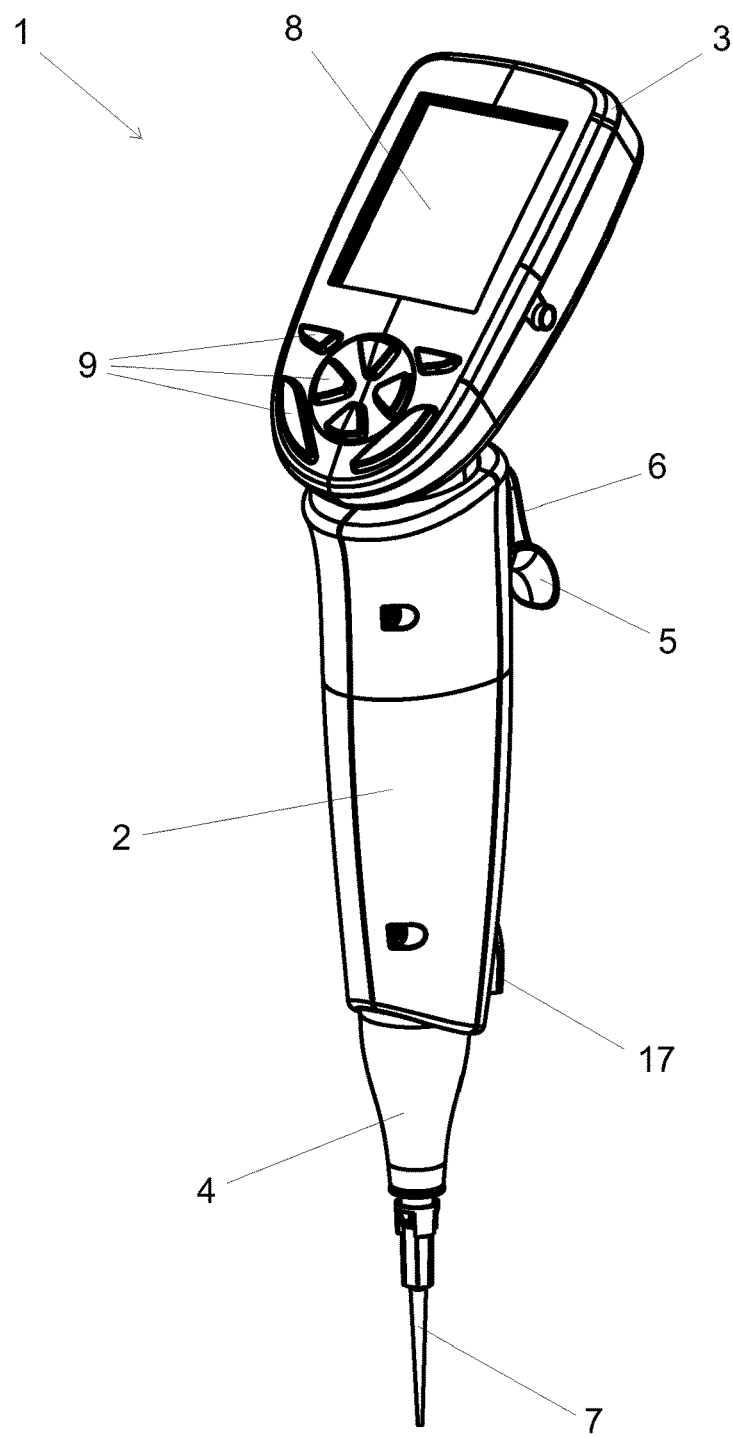
FIG. 1A shows an electronic pipette according to the present invention.
Figures 1B, 1C:
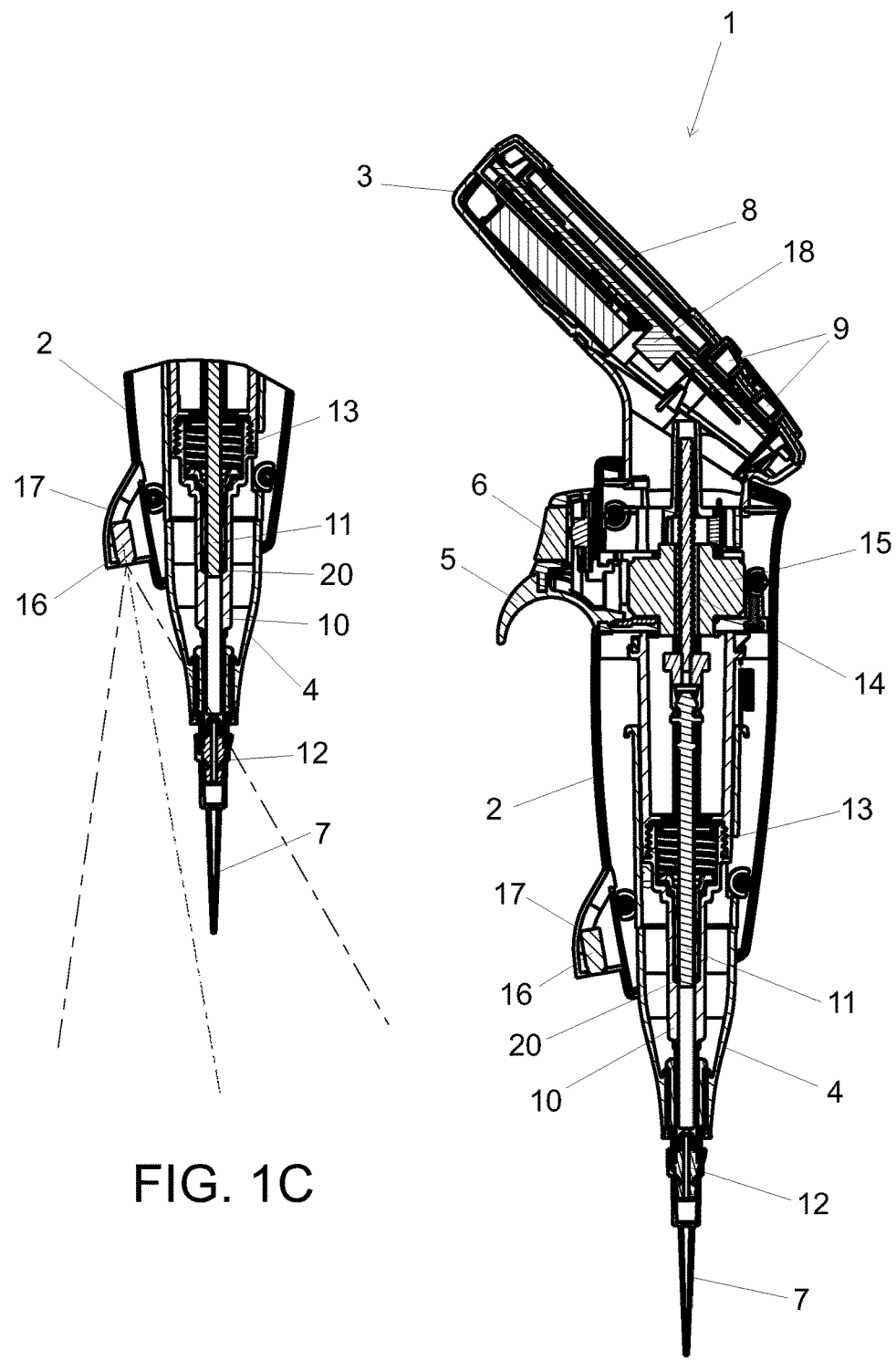
FIG. 1B shows the pipette of FIG. 1A as a cross-section.
FIG. 1C shows area of the cross-section of FIG. 1B.

The electronic pipette 1 of the present invention shown in FIGS. 1A-1C is formed as a handheld entity and the body of which comprises handle portion 2, at upper end of the handle portion tilted display portion 3, and at lower end of the handle portion tip portion 4 of the pipette.

When the pipette 1 is used, it is gripped from the handle portion 2 so that middle finger of the user sets against finger support 5 at the upper part of the handle portion, which leaves index finger of the user free to operate the operating switch 6 of the pipette. To the tip portion 4 is attached detachable pipette tip 7, to which liquid is aspired and from which liquid is dispensed during the use of the pipette 1.

The outer surface of the display portion 3 of the pipette 1 is equipped with a display 8 and operation keys 9, which form the user interface of operating sys-tem of the pipette together with the operating switch 6.

Inside the body of the pipette 1, extending in the area of the handle portion 2 and the tip portion 4 of the pipette, is located a cylinder 10 and inside the cylinder piston 11 movable with respect to the cylinder, which both extend along or parallel with the central axis of the handle portion and/or tip portion of the pipette. From the lower end of the cylinder 11, extends a channel 12 at the bottom end surface of the tip portion 4 for obtaining aspiration and dispensing of liquid to and from the detachable pipette tip 7 by moving the piston 11 inside the cylinder 10. Between surfaces of the cylinder 10 and the piston 11 is located a spring member 13 extending in the length direction of the cylinder and piston for supporting a sealing o-ring 20 between the cylinder and the piston.

The means for moving the piston 11 comprises a linear actuator formed by a threaded rod 14, which extends along or parallel with the central axis of the handle portion 2, and an electric motor 15, which moves the threaded rod in its lengthwise direction through a threaded connection between the unrotating threaded rod and a rotating member of the motor. By moving the threaded rod 14, the piston 11 moves accordingly inside the cylinder 10.

At the lower end of the handle portion 2 is formed a protrusion 17, inside which is set an imaging device element 16, which is able to provide a picture or live feed to the pipette's 1 display 8 and/or save the picture or live feed to the memory of the pipette's electronic control system. The imaging device element 16 can be a single unit, such as a digital camera unit, or it can have an optical lens and an optic fiber to transfer the optical image to a separate optical imaging sensor 18 (e.g., CCD, Charge-Coupled Device), which is preferably located on the electric circuit board of the control system. The picture may also be transferred with a cable or wirelessly to an external display.

The imaging device element 16 is positioned and aimed so, that it shows the pipette tip 7 and area in front of it (FIG. 1C). Thus, the image or image feed from the imaging device element 16 can be used to help the correct positioning of the pipette tip 7. Further, the thus obtained image feed can be used to detect any leftover liquid in the pipette tip 7 or if there are any other problems with the pipette tip, for example. These detection actions can also be implemented automatically by analyzing the image feed from the imaging device element 16 with the electronic operating system.

Figure 2:
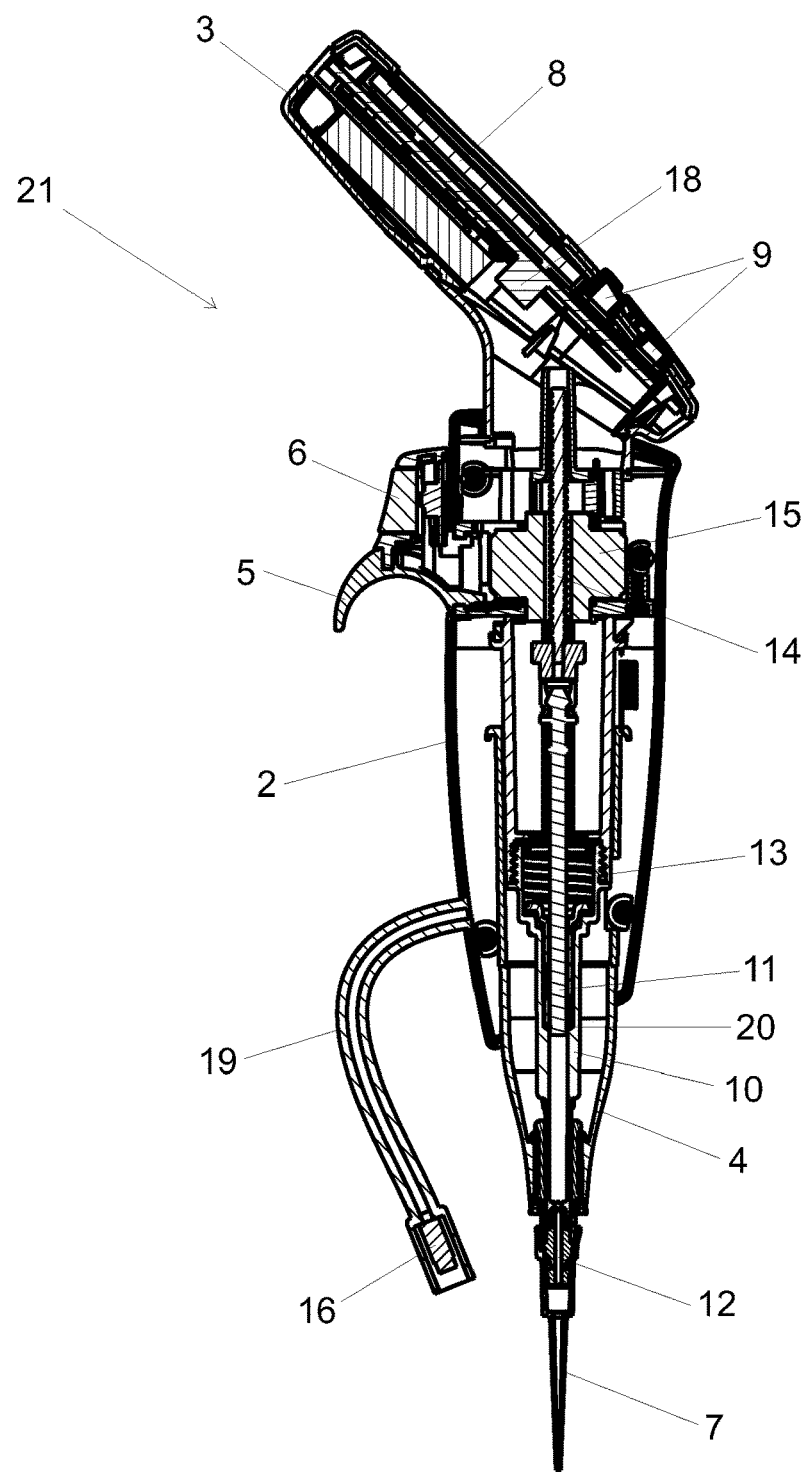
FIG. 2 shows an alternative embodiment of an electronic pipette according to the present invention as a cross-section.

FIG. 2 shows an alternative embodiment of an electronic pipette 21 according to the present invention, where the pipette is otherwise similar than one presented in FIGS. 1A-1C, and the same reference numerals are used for the same parts, with the exception of the connection of the imaging device element 16.

In the embodiment of FIG. 2, the imaging device element 16 is connected to the lower part of the handle portion 2 with a bendable fiber optics wire 22. The bendable fiber optics wire 22 allows free positioning and aiming of the imaging device element 16 so that it can be adjusted to be suitable for different applications and for different pipette tips 7, for example.

Figure 3:
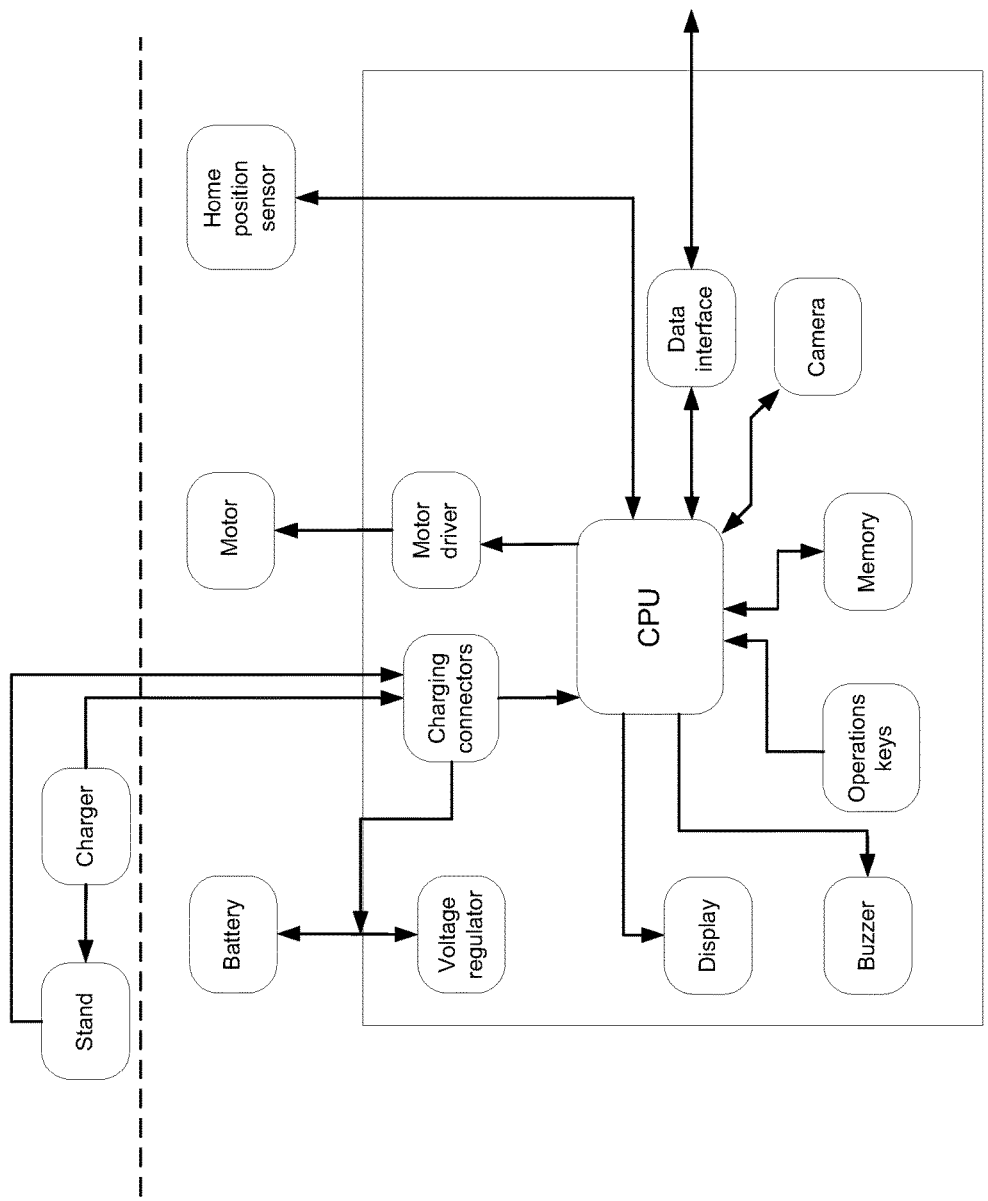
FIG. 3 shows a functional diagram of an electronic pipette according to the present invention.

FIG. 3 shows an example of a functional diagram of an electronic pipette, like the pipettes shown in FIGS. 1A-1C and 2. The operations of the pipette are controlled with a central processing unit (CPU), which is equipped with memory for storing pre-programmed operations and functions. The user gives commands to the CPU through operation keys and selections and information displayed in a display. The CPU is supplied with operating power by a battery and a voltage regulator, which can be recharged with a changer through charging connections when the pipette is placed in its stand. The CPU of the pipette can also be connected to external databases through data interface. The CPU receives information from and controls the pipette's piston home position detector. In accordance with instructions received from the user through the operation keys, the CPU controls the motor of the pipette through a motor driver. The CPU controls a digital camera based on user's input commands, carries out required digital detection and recognition actions, and saves the digital image feed from the camera either to its memory or to external database through data interface. The memory of the pipette may also include a detachable memory module (not shown), such as memory cards, for storing the digital image feed or snapshot images. The CPU also gives alerts through a buzzer in preset situations, or when the CPU notices a problem in a pipetting operation, for example. The dashed line in FIG. 3 presents boundary surface between the pipette itself and the stand of the pipette in which the pipette is placed when not in use.

The specific exemplifying embodiments of the present invention shown in figures and discussed above should not be construed as limiting. A person skilled in the art can amend and modify the embodiments in many evident ways within the scope of the attached claims. Thus, the present invention is not limited merely to the embodiments described above.

What is claimed is:

1. A hand-held pipette, comprising:
   an elongated hand-held body having a handle portion configured for gripping the pipette, a display portion located above the handle portion, and a tip portion located below the handle portion configured for supporting at least one detachable tip;
   a cylinder disposed within the body and having a piston movable inside the cylinder for aspiring and dispensing liquid;
   an imaging device element supported by the pipette and configured for obtaining at least one image, wherein the imaging device element comprises one of a camera unit or an optical imaging sensor including an optical lens that is focused at an area in front of the at least one tip of the pipette and/or at the at least one tip of the pipette; and
   a display supported by the display portion and being configured to display at least one image from the imaging device element.

2. The hand-held pipette according to claim 1, wherein the imaging device element is configured to provide continuous image feed and/or snapshot images.

3. The hand-held pipette according to claim 1, wherein the hand-held pipette is an electronic pipette, comprising:
   a motor for moving the piston inside the cylinder;
   a control system for carrying out pipette operations; and
   a user interface for operating the pipette.

4. The hand-held pipette according to claim 3, wherein the imaging device element, the display for viewing the image from the imaging device element, or the control system of the electronic pipette, is equipped with image recognition.

5. The hand-held pipette according to claim 1, wherein the imaging device element is connected to the handle portion of the pipette, or the imaging device element is connected to the pipette via bendable fiber optics wire.

6. The hand-held pipette according to claim 1, wherein the imaging device element comprises a digital camera.

\* \* \* \* \*